United States Patent [19]

Kalotay

[11] Patent Number: 5,597,949
[45] Date of Patent: Jan. 28, 1997

[54] VISCOSIMETER CALIBRATION SYSTEM AND METHOD OF OPERATING THE SAME

[75] Inventor: Paul Zoltan Kalotay, Lafayette, Colo.

[73] Assignee: Micro Motion, Inc., Boulder, Colo.

[21] Appl. No.: 524,485

[22] Filed: Sep. 7, 1995

[51] Int. Cl.⁶ .................................................. G01N 11/02
[52] U.S. Cl. ............................................. 73/54.01; 73/1 R
[58] Field of Search ............................... 73/54.01, 54.04, 73/54.07, 54.09, 861.04, 1 R, 863.61, 863.71, 863.72, 864.81, 53.04, 54.05, 54.06, 54.43, 61.44, 61.47, 61.78

[56] References Cited

U.S. PATENT DOCUMENTS

| | | | |
|---|---|---|---|
| 3,116,630 | 1/1964 | Piros | 73/54.04 |
| 3,302,451 | 2/1967 | Martin | 73/54.01 X |
| 3,408,859 | 11/1968 | Konen | 73/54.01 |
| 3,465,573 | 9/1969 | Shoemaker | 73/54.01 |
| 3,713,328 | 1/1973 | Aritomi | 73/54.07 X |
| 5,359,881 | 11/1994 | Kalotay et al. | 73/54.02 X |

*Primary Examiner*—Michael Brock
*Attorney, Agent, or Firm*—Duft, Graziano & Forest, P.C.

[57] ABSTRACT

A viscosimeter testing and calibration system (200) includes a main flow line (202), a flow diversion loop (204), a test loop (206), and a purge line (208). The flow diversion loop (204) contains a Coriolis effect viscosimeter (10). The test loop includes a tank (246) that is filled with a standard viscosity liquid (245). A process control unit (210) directs a method of system operation, which can calibrate the viscosimeter (10) without necessitating removal of the viscosimeter (10) from the system (200).

21 Claims, 2 Drawing Sheets

VISCOSIMETER CALIBRATION SYSTEM AND METHOD OF OPERATING THE SAME

FIELD OF THE INVENTION

The present invention pertains to the field of apparatus and methods for conducting rheological measurements on flowing fluids and more particularly to viscosimeter testing and calibration systems. Still more specifically, the viscosimeter testing and calibration system uses a standard viscosity fluid as a basis of comparison.

PROBLEM

Industrial plants commonly use piping systems to carry various materials to points where the materials are used or stored. The flowing materials often lack uniformity from batch to batch, and minor variations in rheology values of the materials can induce significant variations in process efficiencies. Significant classes of rheology values and environmental factors include pressure, temperature, flow rate, fluid density, pH, solids content, and viscosity.

Process conditions can be modified to enhance plant efficiency responsive to changes in material viscosity and other values, however, these process enhancements would require the installation of viscosimeters and other instrumentation to reconnoiter the flowing material. The necessary equipment is often not installed because it is very difficult to maintain. Specifically, an improperly calibrated viscosimeter provides erroneous information which, in turn, induces corresponding process inefficiencies as plant control systems apply incorrect process adjustments. The viscosimeter must, accordingly, be periodically removed from service for calibration and repair in a flow laboratory.

A prime example of the need for improved viscosimeter systems exists in the paper industry. Paper manufacturing plants commonly recycle waste products as boiler fuel in the form of 'black liquor.' These and other black liquor fuels constitute a statistically significant percentage of the total national fuel consumption. Black liquor is a fluid or slurry that typically contains pulp, lignin, sulfuric acid, and water. The fuel mixture is normally heated to a temperature ranging from about 90° C. to 120° C. This temperature reduces the viscosity to an acceptable level that permits use of the black liquor as a fuel. Small particulates can form a colloidal solution with the liquid that is present. Larger particulates can form a fluid-based slurry. The mixture is corrosive and difficult to cleanse from contaminated surfaces.

Conventional boilers designed for use with black liquor fuels have fuel atomizers or spray devices that are designed to accommodate fuel having a viscosity that falls within an optimal viscosity range for peak boiler efficiency. The water content of individual black liquor fuel stocks can vary to produce significant fuel viscosity deviations that fall outside of the optimal viscosity range. These variations occur because black liquor fuel stocks are normally concentrated to remove most of the water, but the degree of concentration varies depending upon prevailing process conditions.

It has heretofore been impractical to use viscosimeters for measuring black liquor fuels. Measurements conducted on hand samples of the fuels fail to produce the desired results because the samples are measured at laboratory conditions that cannot replicate the temperature and flow conditions leading to the boiler. It is also impractical to obtain hand samples for measurement because samples typically cannot be obtained frequently enough to influence process changes throughout the day. Manual sampling and lab-testing create long time delays, which in the face of rapidly changing process conditions make the timely application of laboratory results impractical or impossible. Additionally, it is desirable to have a contained process because the liquor is a hazardous substance.

A variety of viscosimeters are commercially available. Viscosimeters traditionally include ball viscosimeters that determine viscosity as a function of the time that is required for a metal ball to fall through a column of liquid. Other viscosimeters determine viscosity as a function of the fluid shear resistance that is encountered by a rotating body inside a tubular member. Nevertheless, these devices are undesirable for use as in-line viscosimeters in plant piping systems. For example, in-line viscosimeters produce dubious results in black liquor systems due to potential fouling. In-line viscosimeters would have to be removed from their location to a flow laboratory for cleansing and calibration with annoying frequency.

Commercially available Coriolis mass flow meters in combination with simultaneous differential pressure measurement devices can perform viscosity measurements. Coriolis mass flow meters and pressure transducers have no moving parts to be fouled by dirty fluids, and operate with high precision under dynamically changing fluid flow conditions. These meters still require calibration and cleaning from time to time. Thus, the provision of a Coriolis flow meter would fail to eliminate the necessity of removing the meter from in-line service for calibration in a flow laboratory.

It is known to use Coriolis effect mass flowmeters to measure mass flow and other information for materials flowing through a conduit. Such flowmeters are disclosed in U.S. Pat. Nos. 4,109,524 of Aug. 29, 1978, 4,491,025 of Jan. 1, 1985, and Re. 31,450 of Feb. 11, 1982, all to J. E. Smith et al. These flowmeters have one or more flow tubes of straight or curved configuration. Each flow tube configuration in a Coriolis mass flowmeter has a set of natural vibration modes, which may be of a simple bending, torsional or coupled type. Each flow tube is driven to oscillate at resonance in one of these natural modes. Material flows into the flowmeter from a connected conduit on the inlet side of the flowmeter, is directed through the flow tube or tubes, and exits the flowmeter through the outlet side. Meter electronics are used to derive flow information from the meter vibration signals.

SUMMARY OF THE INVENTION

The present invention overcomes the problems outlined above by providing a low maintenance in-line viscosimeter testing and calibration system for use in piping flow systems. The preferred system utilizes a Coriolis viscosimeter in combination with a differential pressure measuring apparatus. Neither one of these transducers have any moving parts to become fouled by dirty fluids or materials.

The viscosimeter test system includes a viscosimeter connected to a main flow line adapted to receive flowing material. A plurality of valve-controlled flow lines or flow loops provide measurement, cleansing, testing, and calibration functions. The loops are preferably 'nested' in the sense that each line circumscribes or occupies a portion of the flow pathway within another line.

A flow diversion line is operably coupled with the main flow line for receipt of flowing material. The viscosimeter is mounted in the flow diversion line, and operates to perform viscosity measurements on material in the flow diversion line. A first valve combination permits selective placement of the system in a normal measurement mode by diverting a portion of the flow from the main flow line through the flow diversion line and the viscosimeter. The primary purpose of the viscosimeter is to conduct these viscosity measurements. A second valve combination permits selective placement of the system in a test mode by preventing diversion of flow through the flow diversion line. Calibration of the viscosimeter is performed, if necessary, after the system is configured for the test mode. The first and second valve combinations can include different flow configurations of three or four way valves.

A test line is operably coupled with the flow diversion line, and includes a reservoir filled with a standard viscosity fluid. A third valve combination permits the standard viscosity fluid to flow through the test line between the reservoir and the viscosimeter when the system is in the test mode.

In preferred embodiments, the viscosimeter is a Coriolis flow meter providing viscosity readings. A computer control unit receives these readings in addition to environmental information (e.g., temperature) that is required to calculate a correlation-derived viscosity for the standard viscosity fluid. The correlation viscosity is compared to the Coriolis viscosity reading from the meter. The computer determines a need to calibrate the meter based upon a difference or percentage difference that exceeds a minimum threshold level. The computer can perform the calibration by adjusting a proportionality constant, and provides the plant operator with a signal indicating a need to service the meter if an attempted calibration fails to produce consistent readings.

The most preferred system includes a purge line to cleanse the flow diversion line prior to its use in the test mode. The purge line is preferably utilized for the blowing of superheated steam, air, or other cleansing agent through the flow diversion line to remove any remaining flow materials that could, otherwise, contaminate the standard viscosity liquid.

The procedure for using the in-line viscosimeter test system advantageously precludes the need for frequent service removal of the viscosimeter. The viscosity is more generally a 'material parameter value,' and the viscosimeter is generally a 'measurement device.' The term "material" is hereby defined to include all fluid based systems at least including liquids, gases, colloids, and slurries. A portion of the material flow is diverted from the main flow line to the flow diversion line. The viscosimeter measurement device determines viscosity as a fluid parameter from the material in the flow diversion line. The flow diversion line is isolated to cease flow of the material through the flow diversion line. Thereafter, the flow diversion line is purged of the material, and fluid is moved from the standard fluid reservoir through the viscosimeter measurement device to determine a test fluid parameter value. The computer calculates a difference between the test parameter value and a standard correlation value for the fluid at prevailing environmental flow conditions. The calculation results can be used to optimize process operations by adjusting the fluid parameter value to fall within an optimal range to optimize plant efficiency with the existing material.

Other salient features, objects, and advantages will become apparent to those skilled in the art as they read the description below in addition to the accompanying drawings.

DETAILED DESCRIPTION OF THE PREFERRED EMBODIMENT

Figure 1:
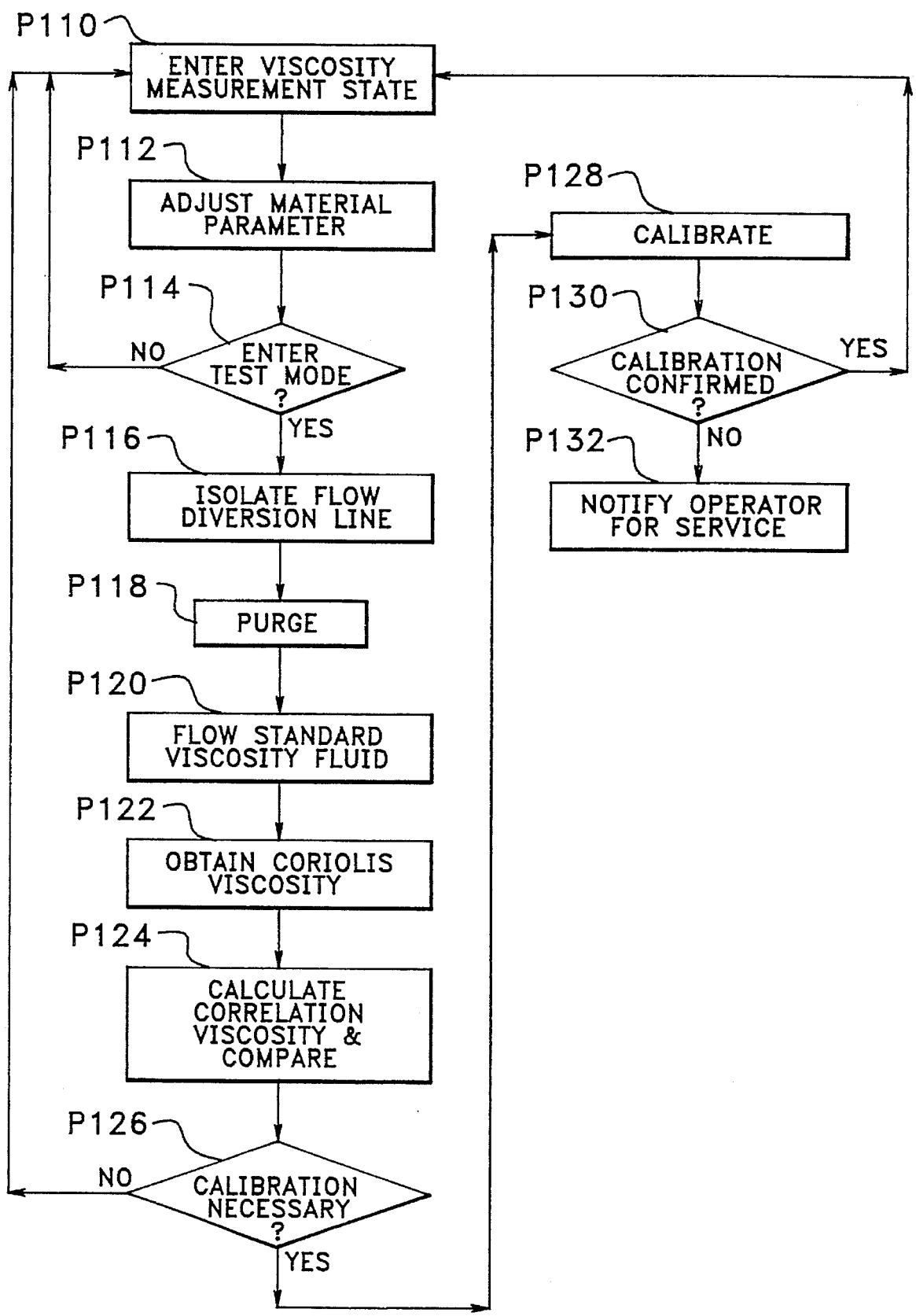
FIG. 1 depicts a schematic process flow chart diagram governing the operation of an in-line viscosimeter testing and calibration system according to the present invention.
Figure 2:
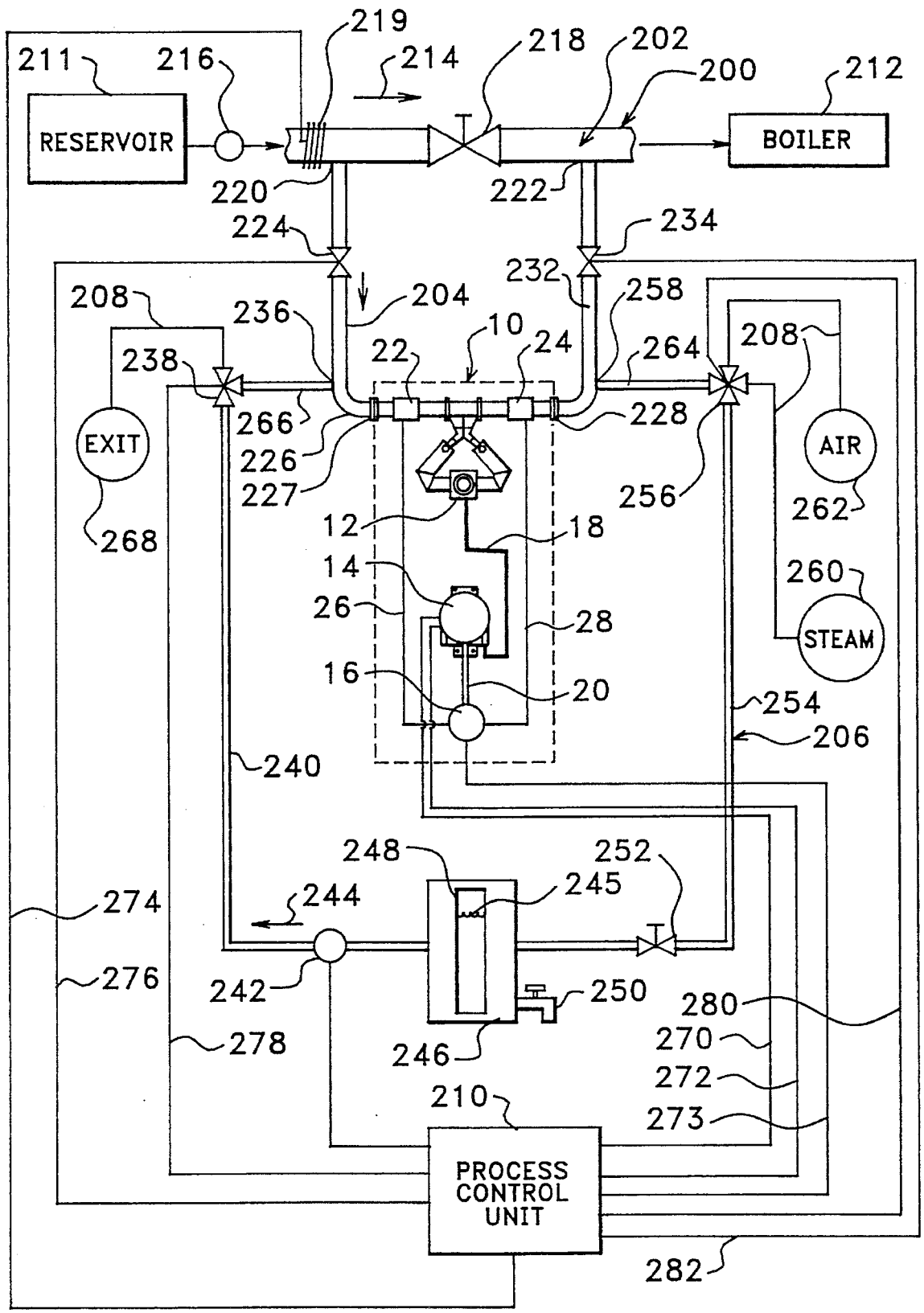
FIG. 2 depicts an in-line viscosimeter testing and calibration system for use according to the process of FIG. 1.

FIG. 2 depicts in-line viscosimeter testing and flow system 200. The major components of system 200 include main flow line 202, slip-stream flow diversion line 204, test line 206, purge line 208, and control unit 210.

Main flow line 202 can be any line that is used to transport a material between a first point and a second point. Line 202 is preferably a fuel line originating at fuel reservoir 211 and terminating at a conventional boiler 212. Flow proceeds through main flow line 202 in the direction of arrow 214 under the force of gravity or with motive assistance from a conventional fuel pump 216. A central valve or choke 218 forms a pressure restriction in line 202. Heating coils 219 circumscribe line 202 at a position upstream of valve 218. Alternatively, heater 219 may be located anywhere in the flow system.

Flow diversion line 204 intersects main flow line 202 at an upstream position 220 and a downstream position 222. Diversion line 204 intersects main flow line 202 at positions 220 and 222 to place valve or choke 218 (a pressure restriction in main flow line 202) between points 220 and 222. Flow diversion line 204 preferably has a reduced diameter with respect to main flow line 202; however, line 204 preferably has an internal diameter that is sized to provide laminar flow within line 204 under all flow conditions. Thus, the determination of appropriate tubing sizes for line 204 will vary as a matter of design choice depending upon the specific application. Conventional flow regime calculations typically involve the application of Reynolds number values, and are well within the capability of those skilled in the art. Line 204 preferably diverts only a portion of the flow in main flow line 202, but can divert all of the flow from line 202 by closure of valve 218.

Flow diversion line 204 includes an upstream valve 224 leading to a curved upstream flange segment 226. Range segment 226 bolts to a corresponding flange component 227, which forms part of the viscosimeter or meter assembly 10.

Assembly 10 is surrounded by a dashed line in FIG. 2 because it can be removed from diversion line 204 as a single piece. Assembly 10 includes a Coriolis mass flowmeter 12, e.g., the commercially available Model CMF025 mass flow meter from Micro Motion of Boulder, Colo. Mass flowmeter 12 is connected to meter electronics 14 through communications lead 18. A particularly preferred form of meter electronics 14 for use with the Model CMF025 mass flowmeter is the remote flow transmitter Model RFT9739, which is also commercially available from Micro Motion, Inc., of Boulder, Colo. Meter electronics 14 communicate with differential pressure transducer or transmitter 16 across lead 20. A suitable device for use as differential pressure measuring transducer 16 is the Model 3051CD, which is commercially available from Rosemount of Minneapolis, Minn. Transducer 16 connects with a pair of conventional pressure transducers 22 and 24 across the corresponding leads 26 and 28. A variety of other commercially available devices may be substituted for the preferred components that are listed by model number hereinabove.

Meter electronics 14 operate to receive measurement signals from mass flowmeter 12, and differential pressure transducer 14. Meter electronics 14 utilize conventional Coriolis processing techniques to facilitate interpretation of these signals as material flow information, e.g., mass flow rate, density, temperature, and viscosity. Meter electronics 14 preferably calculate a viscosity from mass flow information according to the Hagen-Poiseulle capillary tube correlation of Formula (1):

$$\mu = KP\rho/m \qquad \qquad , (1)$$

wherein $\mu$ is absolute viscosity, K is a proportionality constant for the capillary tube; P is a pressure differential across the tube; 82 is density; and m is a mass flow rate for the material. The Hagen-Poiseulle correlation is valid for Newtonian fluids (or near-Newtonian fluids) and laminar flows. Accordingly, it is preferred for those conditions to exist through viscosimeter 12. The approach can be extended to non-Newtonian fluids by solving other characteristic equations corresponding to alternative rheologies.

Assembly 10 includes a downstream flange component 228 which, in turn, bolts to a corresponding curved downstream flange segment 232 leading to the downstream valve 234.

Test line 206 preferably has an internal diameter equal to that of flow diversion line 204. Line 206 connects to upstream curved flange segment 226 at position 236, and proceeds upstream to a three way electronically controlled valve 238. Valve 238 can be opened to provide a through pathway to line section 240 leading to pump 242. Pump 242 is configured to move fluid within line 206 in the direction of arrow 244, and receives fluid 245 from within storage tank 246. Tank 246 need not be pressurized, and can even be vented to atmospheric pressure for the evaporation of fluid contaminants. Tank 246 preferably includes a visual inspection window 248, and a spigot 250 for use in sampling fluid 245 within tank 246.

The fluid 245 within tank 246 is preferably a viscosity standard solution, i.e., it is a commercially available solution having a known viscosity under a variety of flow conditions. The fluid 245 is preferably immiscible and nonreactive with the fluid or material that flows through either main flow line 202 or purge line 208. The immiscibility and nonreactivity prevents contamination or dilution of the standard fluid 245 and facilitates decanting of the standard fluid 245 in the event that contaminants enter tank 246. Dow Corning provides the silicone-based Dow Corning 200 family of fluids, which are particularly preferred standard viscosity solutions for use in black liquor systems. The Dow Corning 200 fluids behave according to the correlation shown below as Formula (2):

$$\log(\mu) = 722.5/T + 0.000032\eta/T + 1.004 \log(\eta) - 2.447 \qquad , (2)$$

wherein $\mu$ is absolute viscosity in cSt of any fluid at a particular temperature T; $\eta$ is a measured viscosity in cSt of the fluid at room temperature (24° C.); and T is temperature in °K. (°C.+273.15).

Valve 252 is provided as a safety measure for manually closing the portion of test line 206 leading to tank 246 during service of tank 246. Valve 252 can also be used to control flow rates in line 206. Alternately pump 242 can be of the variable speed variety. Segment 254 leads to a four way valve 256. Test line Iccp 206 returns to flow diversion line 204 at position 258 on curved flange segment 232.

Purge line 208 originates at superheated steam source 260 or at pressurized air source 262. Sources 260 and 262 can also be any other source of cleansing agent for use in flow diversion line 204. Four way valve 256 has a configuration that closes segment 254 of line 208, and opens segment 264 to one of alternative sources 260 and 262. Line 208 successively proceeds through assembly 10, segment 266, and three way valve 238 to arrive at exit port 268. Port 268 can be any process exit port, e.g., a smokestack, flare, scrubber vent, or even reservoir 211.

Process control unit 210 is preferably a conventional plant control system. Exemplary systems can be purchased on commercial order from national manufacturers such as Honeywell, Allen-Bradley, and Rosemount. The particular choice of control system is not critical to the invention, and may include conventional distributed control systems, or conventional programmable logic control devices, etc. An exemplary control system is the RS3 system that may be obtained from Rosemount of Minneapolis, Minn. Output leads 270 and 272 transmit information to control unit 210 from meter electronics 14. This information preferably includes viscosity and temperature data. Lead 273 transmits differential pressure information to control unit 210. Other leads may be added to additionally transmit mass flow rate, density, or other environmental information pertaining to the fluid or material that is passing through viscosimeter assembly 10.

Leads 276, 278, 280, and 282 respectively connect control unit 210 with the corresponding electrically (or pneumatically) actuated valves 224, 238, 256, and 234, for remote control of the valves.

IIG. 1 depicts a schematic process control diagram that describes the operation of system 200. IIG. 1 is discussed in the context of FIG. 2 reference numbers, but it will be understood that IIG. 1 can be adapted for use in any flow control apparatus. The IIG. 1 process control steps are preferably programmed into control unit 210.

Steps P110 to P114 identify a normal measurement state or mode of viscosimeter operation in which viscosimeter 12 is performing measurements on material diverted from main flow line 202 through assembly 10. In Step P110, viscosimeter assembly 10 is used to obtain a viscosity value from the material that is flowing through flow diversion line 204 from main flow line 202. At this time, valves 238 and 256 are completely closed in all directions. Valves 224 and 234 are open, and valve 218 is partially closed to provide a pressure restriction in main flow line 202, which permits material from line 202 entry into flow diversion line 204. Assembly 10 periodically computes a viscosity value and supplies the value as data to control unit 210. In Step P112, control unit 210 compares the viscosity value from control unit 10 against a preferred value or range of values. Control unit 210 adjusts a fluid parameter value, e.g., temperature, as required to place the viscosity in the proper range. For example, viscosity values that fall above the optimal range are remedied as control unit 210 energizes heating coils 219 or other heaters upstream in the fuel supply lines to heat the material in main flow line 202. The resultant increased temperature induces a corresponding viscosity reduction to place the fuel viscosity within the optimal range.

Step P114 includes a determination of whether the existing normal measurement mode should be terminated for entry into a test mode. Test mode entry can be done periodically according to a clock timer in control unit 210, or responsive to manual operator intervention, Steps P110 through P114 are repeated indefinitely if it is not time to enter the test mode.

Step P116 begins entry into the test mode. Control unit 210 closes valves 224 and 234 to isolate flow diversion line 204 from main flow line 202 by stopping the flow of material from line 202 into line 204. Some of the material will remain within line 204 even after isolation. Therefore, it is a preferred optional step to purge flow diversion line 204 with steam or air in Step P118.

In Step P118, control unit 210 opens valve 256 to communicate one of air source 262 or steam source 260 through valve 256 and into tubing section 264. At the same time, valve 238 opens to communicate tubing section 266 with exit port 268. Valves 256 and 238 remain closed to isolate tubing section 240 from section 266 and to isolate section 254 from section 264. Steam or air is continuously blown through purge line 208 for a sufficient duration of time to substantially cleanse the inside of line 208. At the conclusion of Step P118, control unit 210 closes valve 256 to isolate sources 260 and 262 from tubing section 264. Similarly, valve 238 closes to isolate tubing section 240 from section 266.

The test mode begins at Step P120. Control unit 210 opens valve 238 to connect tubing segment 240 with segment 266. Valve 256 is opened to connect segment 254 with segment 264. Unit 210 activates pump 242 to move the standard viscosity liquid 245 within tank 246 through line 206 and viscosimeter assembly 10. Valve 252 remains open to permit return flow through line 206 entry into tank 246. Pump 242 is preferably activated to flow the standard viscosity liquid 245 through assembly 10 at approximately the same velocity as occurs during actual flow of the material diverted from main flow line 202.

In Step P122, viscosimeter assembly 10 obtains temperature and viscosity readings from the standard viscosity liquid 245, and transmits these readings to control unit 210. Control unit 210 receives these signals and in Step P124 accesses an algorithm according to Formula (2) to calculate a correlation viscosity using the temperature reading from viscosimeter assembly 10. Step P124 includes a comparison of the Coriolis-derived value against the correlation-derived value. A difference or percentage difference that exceeds a minimum threshold level (e.g., a ten percent difference) indicates a possible need to calibrate assembly 10. The precise threshold level will preferably be selected based upon plant operating experience. A threshold level that is too low will require unnecessary calibration. A threshold that is too high will facilitate boiler inefficiency by permitting viscosity to vary outside of the preferred range for operation with a particular boiler.

The result of Step P126 varies depending upon whether the threshold comparison of Step P124 indicated a need to perform a calibration. If the threshold was not reached, Control unit ceases activation of motor 242, closes valve 238 to isolate tubing section 240 from section 266, and closes valve 256 to isolate tubing section 254 from section 264. Steam or air from sources 260 or 262 is then preferably utilized as in Step P118 to purge any remaining amounts of the standard viscosity liquid 245 from purge line 208. This purging action is optional, but can be used as needed to prevent the small remaining portion of standard viscosity liquid 245 from entering boiler 212 where it might have deleterious effects. Control unit 210 completely closes all pathways of valves 238 and 256. Control unit 210 then opens valves 224 and 234 to reestablish the flow situation that existed in Step P110. The comparison input data and results are stored in the computer memory of control unit 210 for later use.

If calibration is required, Step P128 preferably adjusts the proportionality constant K of Formula (1) to reconcile the Coriolis value from Step P122 with the correlation viscosity from Step P124. The adjusted proportionality constant is preferably stored in nonvolatile memory within meter electronics 14.

Step P130 repeats the procedures of Steps P120, P122, P124, and P126. Control unit 210 reestablishes the flow state of Step P110 in the manner described for Step P126 if calibration has caused the coriolis viscosity to agree with the correlation viscosity. On the other hand, the calibration may not work to reconcile the repeat values. In the latter case, Control unit 210 signals the plant operator to service system 200.

Many factors can cause a calibration failure. Viscosimeter assembly 10 will require removal, cleaning and repair in a flow laboratory if it has become plugged, fouled, or broken. The standard viscosity liquid 245 in tank 246 can also be a source of calibration errors. The liquid 245 can degrade or become contaminated over time. These compositional changes in liquid 245 can cause it to behave in a manner that Formula (2) fails to describe. The first course of action in the event of a calibration failure is, accordingly, to obtain a sample of fluid 245 from spigot 250. The sample is transported to a flow laboratory where the thermal and rheological behavior of the fluid is analyzed to ascertain whether the existing fluid behaves as predicted by Formula (2). Contaminated fluid 245 within tank 246 is preferably renewed. Valves 224 and 254 are closed, and viscosimeter assembly 10 can be removed for servicing by releasing connectors (e.g., bolts) at flanges 227 and 228 if the viscosimeter assembly 10 requires repair.

It will be understood that main flow line 202 can conduct any fluid from any source to any point of disposition, and the invention is not limited to fuel feedstocks. Other embodiments could just as well include lines that transport precursors for use in making plastics to reactor vessels, petroleum refinery flow lines, and pharmaceutical plants. It is most preferred that viscosimeter assembly 10 is a Coriolis viscosimeter, however, other viscosimeters can work here as well. These other viscosimeters will become more easily fouled and require more frequent servicing. Other instruments may be substituted for viscosimeter 12 to obtain flow information such as turbidity, mass flow, density, pH, and compositional analysis.

Those skilled in the art will understand that the preferred embodiment described above many be subjected to apparent modifications without departing from the scope and spirit of the invention. The inventor accordingly hereby states his intent to rely upon the Doctrine of Equivalents in order to protect his full rights in the invention.

I claim:

1. An in-line viscosimeter testing system for use in flow systems, comprising:

a main flow line adapted to receive flowing material;

a flow diversion line loop operably connected to said main flow line for transfer of flowing material from said main flow line to said flow diversion line loop and for return of said flowing material from said flow diversion line loop to said main flow line;

a viscosimeter mounted in said flow diversion line loop and operably configured for conducting viscosity measurements on materials flowing through said flow diversion line;

means for selectively diverting said flowing material from said main flow line into said flow diversion line to permit said viscosimeter to perform viscosity measurements on said flowing material;

means for selectively preventing diversion of flow from said main flow line into said flow diversion line to isolate said main flow line from said flow diversion line;

a purge line occupying a portion of said flow diversion line and providing means for purging said flow diversion line of said flowing material when said selectively preventing means is isolating said main flow line from said flow diversion line;

a test line loop including a reservoir containing a standard viscosity fluid, said test line loop being operably connected to said flow diversion line for supplying said standard viscosity liquid to said flow diversion line and said viscosimeter when said selectively preventing means is isolating said main flow line from said flow diversion line;

means for selectively flowing said standard viscosity fluid through said test line loop between said reservoir and said viscosimeter to permit said viscosimeter to perform viscosity measurements on said standard viscosity fluid when said flow diversion line is isolated from said main flow line; and means for comparing said viscosity measurements performed on said standard viscosity fluid against standard correlation values for said standard viscosity fluid.

2. The viscosimeter test system as set forth in claim 1, said viscosimeter including a Coriolis flow meter and a differential pressure sensor.

3. The viscosimeter test system as set forth in claim 2, said Coriolis flow meter including computing means for converting measurement signals obtained from said standard viscosity fluid in said flow diversion line into a viscosity value.

4. The viscosimeter test system as set forth in claim 3, including means for calculating a difference between said viscosity value and a correlation-derived viscosity value representative of environmental use conditions for said standard viscosity liquid.

5. The viscosimeter test system as set forth in claim 4, including means for calibrating said viscosimeter when said difference exceeds a threshold level.

6. The viscosimeter as set forth in claim 3 said computing means including a Hagen-Poiseulle algorithm.

7. The viscosimeter test system as set forth in claim 1 wherein said means for selectively preventing diversion of flow includes a first valve positioned in said flow diversion line at an upstream flow position relative to said viscosimeter and a second valve positioned in said flow diversion line at a downstream flow position relative to said viscosimeter.

8. The viscosimeter test system as set forth in claim 1, said reservoir including a visual inspection port.

9. The viscosimeter test system as set forth in claim 1, said reservoir including a spigot configured to provide samples of said standard viscosity fluid within said reservoir.

10. The viscosimeter test system as set forth in claim 1 wherein said test line loop includes means for returning said standard viscosity liquid to said reservoir after said standard viscosity liquid has passed through said viscosimeter.

11. The viscosimeter test system as set forth in claim 1 wherein said purge line is a steam injection line.

12. The viscosimeter as set forth in claim 11, including a three way valve operably positioned to control flow through said steam injection line and said test line.

13. The viscosimeter test system as set forth in claim 11, said purging means including an air injection line.

14. The viscosimeter test system as set forth in claim 13, including a four-way valve operably positioned to control flow through said steam injection line, said test line, and said air injection line.

15. The viscosimeter test system as set forth in claim 1, said flowing means including means for moving said standard viscosity fluid through said test line loop, when said flow diversion line is isolated from said main flow line, at a rate approximating a mass rate of flow through said viscosimeter when said flow diversion line is not isolated from said main flow line.

16. The viscosimeter test system as set forth in claim 15, said standard viscosity fluid having a density approximating that for material within said main flow line.

17. An in-line viscosimeter test procedure, comprising the steps of:

providing a series of nested tubing loops including a main flow line, a flow diversion line loop including a measurement device connected to said main flow line, a test line loop including a standard liquid reservoir connected to said flow diversion line loop, and a purge line connected to said flow diversion line loop;

flowing material through said main flow line;

diverting a portion of said material from said main flow line to said flow diversion line loop;

determining a material parameter value from said material in said flow diversion line loop through use of said measurement device;

isolating said flow diversion line loop to cease flow of said material through said flow diversion line loop; thereafter purging said flow diversion line loop of said material;

moving standard liquid from said standard liquid reservoir through said measurement device to determine a test parameter value; and calculating a difference between said test parameter value and a standard correlation value for said standard liquid at environmental conditions.

18. The procedure as set forth in claim 17, wherein said measurement device is a Coriolis viscosimeter.

19. The procedure as set forth in claim 17, including a step of calibrating said viscosimeter when said difference exceeds a threshold level.

20. The procedure as set forth in claim 17, wherein said determining step includes a step of adjusting said material parameter value for maintenance of said material parameter value within a tolerance range.

21. The procedure as set forth in claim 20, wherein said determining step includes a step of adjusting a heater responsive to said material parameter value.

* * * * *